United States Patent [19]

Okumura et al.

[11] 4,327,231
[45] Apr. 27, 1982

[54] PROCESS FOR THE PRODUCTION OF TERTIARY ALCOHOLS

[75] Inventors: Yoshiharu Okumura, Kawagoe; Hiroshi Furukawa; Katsumi Kaneko, both of Ooi, all of Japan

[73] Assignee: Toa Nenryo Kogyo Kabushiki Kaisha, Tokyo, Japan

[21] Appl. No.: 126,822

[22] Filed: Mar. 3, 1980

[30] Foreign Application Priority Data

Apr. 27, 1979 [JP] Japan .................. 54-51463

[51] Int. Cl.³ .................................. C07C 29/04
[52] U.S. Cl. ........................... 568/899; 568/895; 568/896; 568/897; 568/898; 568/900; 568/901
[58] Field of Search ..................... 568/895–901

[56] References Cited

U.S. PATENT DOCUMENTS

| 3,257,469 | 6/1966 | Kovach | 568/899 |
| 3,285,977 | 11/1966 | Henke et al. | 568/896 |
| 3,646,237 | 2/1972 | Horie et al. | 260/677 A |
| 3,965,039 | 6/1976 | Chaplits et al. | 252/426 |
| 4,012,456 | 3/1977 | Chaplits | 568/899 |
| 4,087,471 | 5/1978 | Bowman et al. | 568/899 |
| 4,096,194 | 6/1978 | Moy et al. | 568/899 |

FOREIGN PATENT DOCUMENTS

| 875433 | 7/1979 | Belgium . |
| 920616 | 2/1973 | Canada . |
| 1443009 | 7/1976 | United Kingdom . |
| 1443106 | 7/1976 | United Kingdom . |
| 1451158 | 9/1976 | United Kingdom . |
| 1518461 | 7/1978 | United Kingdom . |
| 2003141 | 3/1979 | United Kingdom . |

OTHER PUBLICATIONS

Odioso et al., "I. & E. C.", vol. 53, No. 3, Mar. 1961, pp. 209-211.

Primary Examiner—Joseph E. Evans
Attorney, Agent, or Firm—Rebecca Yablonsky

[57] ABSTRACT

Tertiary alcohols are produced by the hydration of an isoolefin in the presence as catalyst of an acidic cation exchange resin such as a sulfonated styrene-divinylbenzene copolymer, and a polyhydric neo-type alcohol such as neopentyl glycol. The process is useful for separating isobutylene from a hydrocarbon mixture containing its isomers via preparation of the alcohol, separation from the unreacted hydrocarbons and dehydration of the tertiary butyl alcohol to isobutylene.

9 Claims, 1 Drawing Figure

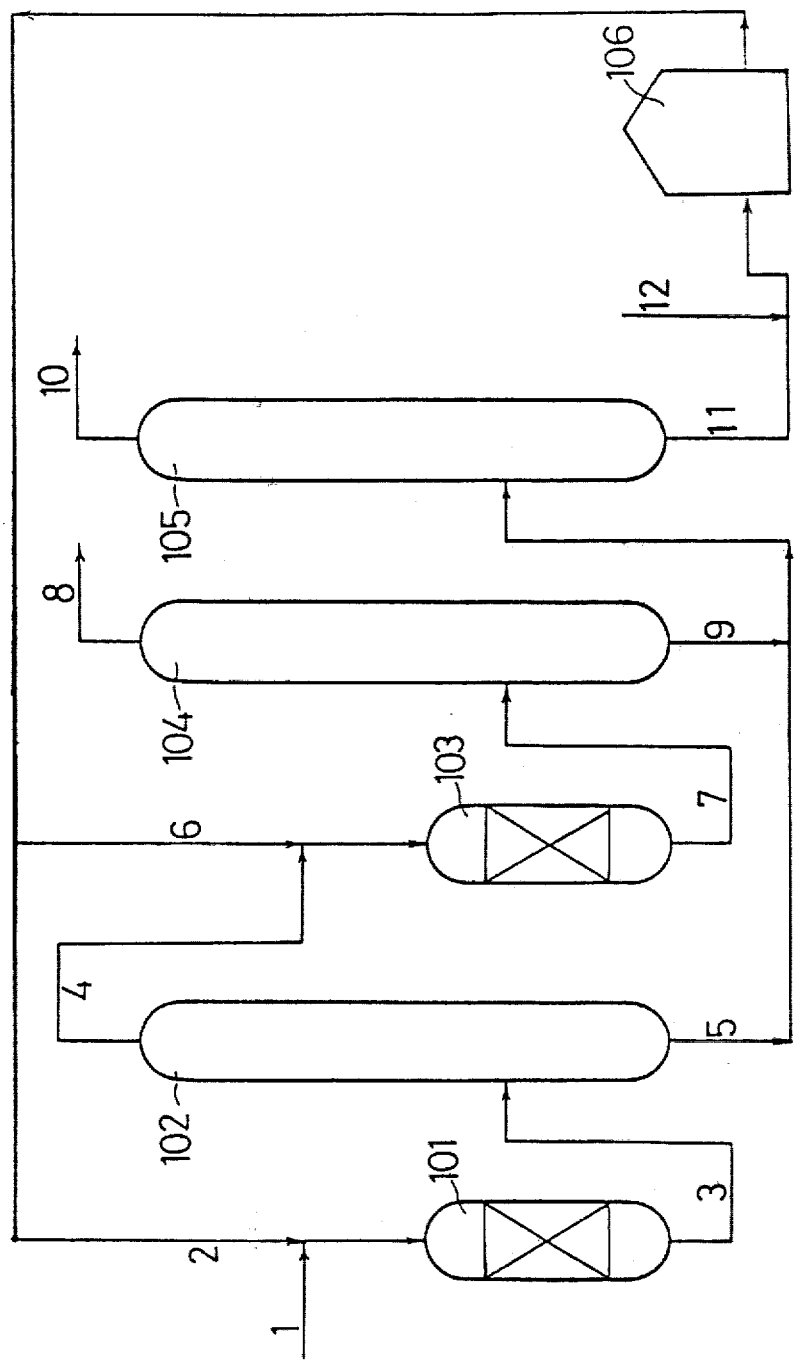

PROCESS FOR THE PRODUCTION OF TERTIARY ALCOHOLS

BACKGROUND OF THE INVENTION

1. Field of the Invention

This invention relates to a process for producing tertiary butyl alcohol (TBA) in a higher yield than previously obtainable by reacting isoolefins, in particular isobutylene, with water and more particularly it is concerned with a process for producing TBA in a higher yield by reacting isobutylene with water in the presence of a neo-type polyhydric alcohol or its derivative using a solid catalyst, preferably a acid type cation exchange resin.

2. Description of the Prior Art

For the production of TBA by hydration of isobutylene, there have been proposed an indirect hydration method comprising absorbing isobutylene in sulfuric acid and hydrolyzing the formed sulfuric acid ester and a direct hydration method comprising using a solid acid or an acidic aqueous solution as a catalyst.

Of these methods, the method using an aqueous solution of sulfuric acid has the disadvantage that large amounts of by-products are formed through dimerization or trimerization of isobutyelen and that there are problems of the corrosion of the apparatus and the treatment of the waste sulfuric acid. In most of the direct hydration methods using a solid acid or acidic aqueous solution as a catalyst, on the other hand, some activity appears only at a high temperature such as about 200° C. or higher. Since the equilibrium of the hydration reaction is disadvantageous for the formation of the alcohol with the rise of temperature, it is necessary to conduct the reaction under a very high pressure in order to obtain a sufficient yield at such a high temperature. In this respect, a sulfonic acid type ion exchange resin is a good catalyst capable of advancing the reaction at a relatively low temperature and low pressure. A number of methods using the same have been proposed.

For example, "Industrial and Engineering Chemistry" Vol. 53, No. 3, page 209-211 describes a method wherein isobutylene is continuously hydrated using an ion exchange resin as a catalyst, but this method is not always satisfactory because water and isobutylene form a heterogeneous system and thus give an insufficient reaction speed and yield. For the purpose of solving this problem, there have been proposed a method comprising reacting isobutylene or an isobutylen-containing hydrocarbon with an aqueous solution of an organic acid using an acidic ion exchange agent as a catalyst (Japanese Patent Application (OPI) No. 32116/1975 and Japanese Patent Publication No. 14044/1978); a method comprising carrying out the reaction with addition of a monohydric alcohol to the reaction system and using a similar catalyst (Japanese Patent Application (OPI) No. 137906/1975) and a method comprising carrying out the reaction with addition of glycol, glycol ether or glycol diether to the reaction system (Japanese Patent Application (OPI) No. 59802/1976 and U.S. Pat. No. 4,096,194).

In these methods for producing TBA by directly hydrating isobutylene, however, some improvement in reaction speed is found and, on the other hand, by-products are formed such as adducts of isobutylene with organic acids or organic solvents which are added to the reaction system. These by-products and organic solvents added to the reaction system make it difficult to separate and purify TBA by distillation utilizing the difference of their boiling points. In the case of using organic acids such as acetic acid, the apparatus tends to become corroded.

SUMMARY OF THE INVENTION

Applicants have made various studies to solve the above described problems and have found that the side reactions can be suppressed and the reaction rate and conversion ratio can be markedly promoted by adding a neo-type polyhydric alcohol to water in the hydration reaction using an acid-type cation exchange resin. The present invention is based on this finding.

That is to say, the present invention provides a process for producing TBA comprising reacting a $C_4$ or $C_5$ isoolefin or an isoolefin-containing hydrocarbon mixture, preferably isobutylene or an isobutyelen-containing hydrocarbon mixture, with water in the presence of a solid catalyst, preferably an acid-type cation exchange resin, characterized in that a neo-type polyhydric alcohol or derivative thereof is included in the reaction system.

The quantity of isobutylene or the isobutylene content in an isobutyene-containing hydrocarbon mixture, used in the present invention, is not particularly limited. Generally, the isobutylene-containing hydrocarbon mixture comprises predominantly $C_4$ hydrocarbons, for example, isobutylene, n-butylene and butane and, optionally, some amounts of $C_3$ or $C_5$ hydrocarbons. On a commercial scale, isobutylene-containing $C_4$ hydrocarbon mixtures obtained by steam cracking or catalytic cracking of petroleum fractions, are used.

BRIEF DESCRIPTION OF THE DRAWING

The accompanying drawing is a flow diagram which illustrates carrying out the process of the present invention continuously.

DETAILED DESCRIPTION

The neo-type polyhydric alcohol or derivative thereof used in the present invention is illustrated in the following:

The neo-type polyhydric alcohol is represented by the following general formula,

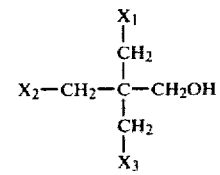

in which $X_1$, $X_2$ and $X_3$ are selected from the group consisting of hydrogen, hydroxyl group and organic groups such as alkyl, especially methyl, aryl, alkoxy, substituted alkoxy and ester groups and at least one of $X_1$, $X_2$ and $X_3$ is a hydroxyl group or a hydroxyl-containing group. Preferred polyhydric alcohols are those in which at least one of $X_1$, $X_2$ and $X_3$ is a hydroxyl group, or their ethers with the same or a different alcohol. Examples of the polyhydric alcohol having such a structure are:

(1) Pentaerythritol

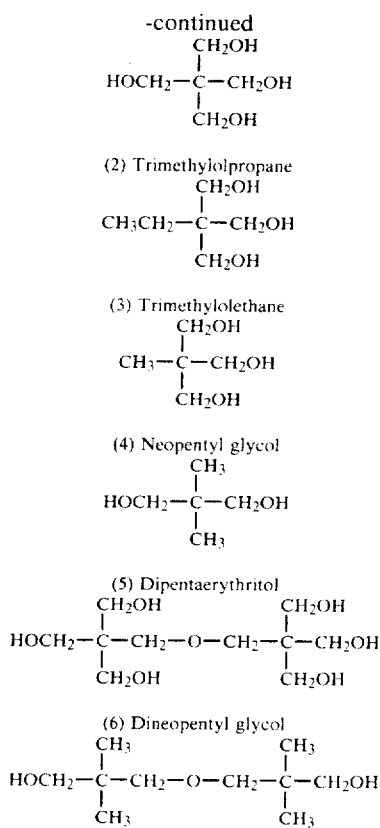

(2) Trimethylolpropane (3) Trimethylolethane (4) Neopentyl glycol (5) Dipentaerythritol (6) Dineopentyl glycol As the derivative of the neo-type polyhydric alcohol, there can be used esters or partially esterified products thereof or their ethers such as the ether-dimers as described above. The neo-type polyhydric alcohols or their derivatives can of course be used in combination.

The neo-type polyhydric alcohol or derivative thereof is ordinarily used in the form of a solution in water but it is not always required that it should be completely dissolved therein. As the added quantity of the neo-type polyhydric alcohol or derivative thereof is increased, in general, the rate of formation of TBA increases but the viscosity of the solution becomes greater also. Accordingly, the said compound is generally added in a proportion of 5 to 800 parts by weight, preferably 10 to 400 parts by weight, to 100 parts by weight of water.

The solid catalyst used in the present invention includes preferably strongly acidic cation exchange resins, for example, sulfonated polystyrene resins in which sulfonic acid groups are introduced into a base of a copolymer of styrene and divinylbenzene; phenolsulfonic acid resins in which sulfonic acid groups are introduced into a condensate of phenol and formaldehyde; and perfluorosulfonic acid resins consisting of copolymers of sulfonated vinyl ether fluoride and fluorocarbon, which are preferably of a gel type, macroporous type or macroreticular type. In addition, other solid catalysts for hydration can be used, for example, oxide type catalysts such as alumina, silica alumina, silica gel, zeolites, mordenites, kaolin, oxides of metals such as tungsten, thorium, zirconium, molybdenum, zinc, titanium and chromium; supported ones of these oxides; mineral acid catalysts such as supported phosphoric acid; heteropoly acid catalysts such as supported silicotungstic acid; sulfides such as sulfides of nickel and nickel-tungsten or supported ones of these sulfides; and metal sulfates such as aluminum sulfate.

The quantity of the catalyst depends upon how it is used, that is, whether it is used in the form of a suspension or a fixed bed. In the former case, the quantity of the catalyst is preferably 0.1 to 10% by weight of an aqueous solution of a neo-type polyhydric alcohol.

The molar ratio of water to isobutylene ranges preferably from 1 to 10 since if less than 1, the conversion ratio is lowered, while if too large, the efficiency of a reactor is lowered.

The reaction temperature is generally 30° to 150° C., preferably 50° to 120° C.

The reaction pressure may be normal pressure, but the reaction is preferably operated under a pressure corresponding to the vapor pressure of a hydrocarbon mixture as a starting material at the reaction temperature or under a pressure somewhat higher than the vapor pressure.

The form of reactor to be used may be of a batchwise type, but, in general, it is of a continuous type with an acid-type cation exchance resin in the form of a fixed bed.

The reaction time is generally in the range of 20 minutes to 10 hours in the case of a batchwise type and the liquid hourly space velocity (LHSV) of a hydrocarbon is ordinarily 0.3 to 10 $hr^{-1}$ in the case of a continuous type.

One embodiment of the process of the present invention will now be illustrated with reference to the accompanying drawing. In this embodiment, isobutylene from an isobutylene-containing hydrocarbon mixture is continuously converted into TBA and separated.

The system comprises mainly first and second reactors 101 and 103 filled with a catalyst, distilling columns 102 and 104 for the separation of unreacted hydrocarbons, a distilling column 105 for the separation of TBA and a storage tank 106 of an aqueous solution of neo-type polyhydric alcohol. A starting hydrocarbon mixture and an aqueous solution of neo-type polyhydric alcohol are fed to the first reactor respectively from a pipe 1 and a pipe 2. The reaction liquor containing TBA is withdrawn from the bottom of the first reactor 101 and fed through a pipe 3 to the distilling column 102 for the separation of unreacted hydrocarbons. A hydrocarbon mixture containing unreacted isobutylene is withdrawn from distilling column 102 through a pipe 4 and fed with the aqeuous solution of neo-type polyhydric alcohol from a pipe 6 to the second reactor 103. A TBA-containing reaction liquor is discharged from the bottom of the second reactor 103 and fed to the distilling column 104 for the separation of hydrocarbons via a line 7, from which an unreacted hydrocarbons mixture is taken via line 8. TBA-containing liquors withdrawn from lines 5 and 9 are fed to the distilling column 105 for the separation of TBA, from which crude TBA is taken through line 10. An aqueous solution of neo-type polyhydric alcohol is taken via line 11, mixed with water from line 12 and reused for the reaction through the storage tank 106. Removal of water from the crude TBA is carried out in conventional manner.

According to the process of the present invention, the rate of the hydration reaction of isobutylene and the conversion ratio thereof can be increased markedly with suppression of side reactions, thus allowing obtaining TBA in high yield. Moreover, a neo-type polyhydric alcohol having a conderably high boiling point can readily be separated and purified from TBA by distillation and thus the reuse thereof is simplified.

By means of the present process isobutylene can be isolated from an isobutylene-containing hydrocarbon mixture. That is to say, isobutylene in an isobutylene-containing hydrocarbon mixture is preferentially converted into TBA according to this process and the unreacted hydrocarbon mixture is then separated, after which TBA is dehydrated in known manner to give isobutylene. Isobutylene of high purity can be obtained in this way.

The present invention will further be illustrated in detail by the following examples and comparative examples, in which parts are by weight and percentages are by mole unless otherwise indicated.

EXAMPLES 1–9

Using an autoclave equipped with a stirrer and a cation exchange resin of macroreticular type (Amberlite 15, commercial name) consisting of a sulfonated styrene-divinylbenzene copolymer as a catalyst, hydration reactions of isobutylene (99.5%) and an isobutylene-containing $C_4$ hydrocarbon (isobutylene 41.0%, n-butylenes 43.0%, butanes 16.0%) were carried out with solutions of neo-type polyhydric alcohols in water under conditions as shown in Table 1. After the reactions, the reaction products were rapidly cooled and subjected to analysis by gas chromatography to obtain the yields of TBA and by-products. The results are shown in Table 1.

TABLE 1

| Ex. | Alcohol | Alcohol (g) | Water (g) | Isobutylene Content in Starting Hydrocarbon (%) | Amount of Isobutylene (mol) | Amount of Catalyst (g) | Reaction Temperature (°C.) | Reaction Pressure (Kg/cm$^2$) | Reaction Time (hr) | Yield of TBA (%) | Yield of by-products (%) |
|---|---|---|---|---|---|---|---|---|---|---|---|
| 1 | Neopentylglycol | 200 | 200 | 99.5 | 3.0 | 20 | 80 | 12 | 0.5 | 25.3 | 0.1 |
| 2 | Neopentylglycol | 300 | 100 | 99.5 | 3.0 | 20 | 70 | 9 | 0.5 | 18.5 | 0.1 |
| 3 | Trimethylolpropane | 200 | 200 | 41.0 | 1.0 | 20 | 80 | 12 | 0.5 | 19.5 | 0.1 |
| 4 | Trimethylolpropane | 100 | 300 | 99.5 | 3.0 | 20 | 80 | 12 | 1.0 | 29.2 | Trace |
| 5 | Pentaacrythritol | 40 | 360 | 99.5 | 3.0 | 20 | 80 | 12 | 1.0 | 16.1 | No |
| 6 | Trimethylolpropane | 100 | 150 | 41.0 | 1.0 | 20 | 70 | 9 | 0.5 | 17.3 | 0.3 |
|   | Neopentylglycol | 150 | | | | | | | | | |
| 7 | Trimethylolpropane | 200 | 200 | 99.5 | 3.0 | 15 | 80 | 12 | 4.0 | 92.1 | 0.3 |
| 8 | Neopentylglycol | 250 | 150 | 99.5 | 3.0 | 15 | 60 | 7 | 5.0 | 93.2 | 0.4 |
| 9 | Pentaerythritol | 50 | 150 | 41.0 | 1.0 | 15 | 80 | 12 | 5.0 | 80.2 | 0.5 |
|   | Neopentylglycol | 200 | | | | | | | | | |

(Note) Yield: mole % based on isobutylene fed.

Comparative Examples 1–8

In the hydration reaction of isobutylene using the same reactor, catalyst and starting hydrocarbon as those of Examples 1–9, comparison tests were carried out with no addition of organic solvent to the reaction system and with addition of other organic solvents in place of the neo-type polyhydric alcohols. The experimental conditions and results are shown in Table 2.

The yields of TBA and by-products were obtained in a manner analogous to Examples 1–9.

TABLE 2

| Ex. | Solvent | Amount of Solvent (g) | Water (g) | Isobutylene Content in Starting Hydrocarbon (%) | Amount of Isobutylene (mol) | Amount of Catalyst (g) | Reaction Temperature (°C.) | Reaction Pressure (Kg/cm$^2$) | Reaction Time (hr) | Yield of TBA (%) | Yield of by-products (%) |
|---|---|---|---|---|---|---|---|---|---|---|---|
| 1 | None | — | 400 | 99.5 | 3.0 | 20 | 80 | 12 | 1.0 | 8.3 | 0.5 |
| 2 | None | — | 400 | 41.0 | 1.5 | 15 | 80 | 12 | 8.0 | 25.1 | 1.3 |
| 3 | Methanol | 200 | 200 | 99.5 | 3.0 | 20 | 80 | 12 | 1.0 | 16.7 | 4.5 |
| 4 | Ethyl Cellosolve | 200 | 200 | 99.5 | 3.9 | 20 | 80 | 12 | 1.0 | 10.7 | 2.4 |
| 5 | Ethylene Glycol | 200 | 200 | 99.5 | 3.0 | 20 | 80 | 12 | 1.0 | 6.2 | 1.2 |
| 6 | Diethylene Glycol | 200 | 200 | 99.5 | 3.0 | 20 | 80 | 12 | 1.0 | 7.9 | 1.4 |
| 7 | Neopentyl Alcohol | 200 | 200 | 99.5 | 3.0 | 20 | 80 | 12 | 1.0 | 6.8 | 0.2 |
| 8 | Acetic Acid | 200 | 200 | 99.5 | 3.0 | 20 | 80 | 12 | 1.0 | 17.2 | 2.4 |

(Note) Yield: mole % based on isobutylene fed

EXAMPLE 10

This example describes a process comprising continuously hydrating isobutylene in an isobutylene-containing C$_4$ hydrocarbon mixture and separating TBA using the apparatus shown in the accompanying flow diagram.

To a first reaction 101 were respectively fed a starting C$_4$ hydrocarbon mixture (isobutylene 19.8%, n-butenes 32.0%, butanes 48.2%), obtained from a catalytic cracking apparatus, at a rate of 8415 parts/hr. from a pipe 1 and a 55% by weight aqueous solution of neopentyl glycol at a rate of 7200 parts/hr. from a pipe 2. The first reactor 101 was filled with the same catalyst as that used in Examples 1–9 and the hydration reaction was carried out under conditions of a temperature of 90° C., pressure of 16 Kg/cm$^2$ and liquid space velocity of LHSV 2.0 hr$^{-1}$. A liquor containing 11.6% of TBA, discharged from the first reactor 101, was fed at a rate of 15615 parts/hr. to a first distilling column 102 for the separation of hydrocarbons via a pipe 3. An unreacted hydrocarbon mixture via a pipe 4 and an aqueous neopenyl glycol solution containing 21.1% of TBA via a pipe 5 at a rate of 8566 parts/hr. were respectively withdrawn. The unreacted isobutylene-containing hydrocarbon mixture (isobutylene 4.3%, n-butenes 38.2%, butanes 57.5%) via the pipe 4 at a rate of 7049 parts/hr. and the 55% by weight aqueous solution of neopentyl glycol via a pipe 6 at a rate of 3600 parts/hr. were respectively fed to a second reactor 103 (filled with the same catalyst as that of the first reactor 101) in which the hydration reaction was carried out under conditions of a temperature of 70° C., pressure of 11 Kg/cm$^2$ and liquid space velocity LHSV of 1.0 hr$^{-1}$. A liquor containing 3.1% of TBA, discharged from the second reactor 103, was fed via line 7 at a rate of 10649 parts/hr. to a second distilling column 104 for the separation of hydrocarbons, from which an unreacted hydrocarbon mixture (isobutylene 0.6%, n-butenes 39.6%, butanes 59.8%) via line 8 at a rate of 6797 parts/hr. and an aqueous neopentyl glycol solution containing 8.6% of TBA via line 9 at a rate of 3852 parts/hr. were respectively withdrawn. The liquors containing TBA withdrawn via the line 5 from the first distilling column 102 and via line 9 from the second distilling column 104 were combined and fed to a third distilling column 105 for the separation of TBA, from which a crude TBA (TBA 88.2% water 11.8%) via line 10 at a rate of 2456 parts/hr. and an aqueous solution of neopentyl glycol via line 11 at a rate of 9994 parts/hr were respectively withdrawn. The aqueous solution of neopentyl glycol withdrawn via line 11 was mixed with water at a rate of 806 parts/hr. via line 12, delivered to a storage tank 106 of the 55% by weight aqueous solution of neopentyl glycol and then recycled to each of the reactors.

The yields of TBA were 82.0% for the first reactor 101 and 84.0% for the second reactor 103.

What is claimed is:

1. In a process for the production of tertiary alcohols by causing an isoolefin or a hydrocarbon mixture containing an isoolefin to react with water in the presence of a solid catalyst, the improvement which comprises carrying out the reaction in the presence of 5 to 800 parts by weight per 100 parts by weight of water of a neo-type polyhydric alcohol or derivative thereof.

2. In a process for the production of tertiary alcohols by causing an isoolefin or a hydrocarbon mixture containing an isoolefin to react with water in the presence of an acidic cation exchange resin, the improvement which comprises carrying out the reaction in the presence of 5 to 200 parts by weight per 100 parts by weight of water of a neo-type polyhydric alcohol having the general formula

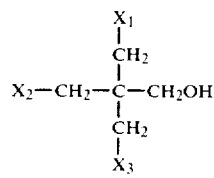

in which $X_1$, $X_2$ and $X_3$ are selected from the group consisting of hydrogen, hydroxyl, alkyl, aryl, alkoxy, substituted alkoxy and ester groups and at least on of $X_1$, $X_2$ and $X_3$ is a hydroxyl or hydroxyl-containing group; or the esters or partially esterified products thereof or ethers thereof.

3. The process as set forth in claim 2 in which $X_1$, $X_2$ and $X_3$ are selected from the group consisting of hydrogen, hydroxyl and methyl and at least one is hydroxyl.

4. The process as set forth in claim 2 in which the polyhydic alcohol is selected from the group consisting of pentaerythritol, trimethylolpropane, trimethylolethane, neopentyl glycol, the ether-dimers of said polyhydric alcohols and mixtures thereof.

5. The process as set forth in claims 2, 3 or 4 in which the resin used is a sulfonated resin.

6. The process as set forth in claims 2, 3 or 4 in which the resin used is a sulfonated styrene-divinylbenzene copolymer.

7. The process as set forth in claims 2, 3 or 4 in which the feed contains isobutylene and tertiary butyl alcohol is recovered as product.

8. The process as set forth in claim 2 in which the feed comprises isobutylene in a hydrocarbon mixture, the resin used is a sulfonated styrene-divinylbenzene copolymer and tertiary butyl alcohol produced by hydration is recovered in a substantially purified form.

9. The process as set forth in claim 2 in which the hydrocarbon mixture comprises predominantly C$_4$ hydrocarbons including isomers of isobutylene.

* * * * *